(12) United States Patent
Nakaguma et al.

(10) Patent No.: US 11,441,120 B2
(45) Date of Patent: Sep. 13, 2022

(54) CELL CULTURE SUBSTRATE

(71) Applicant: FUJIFILM Corporation, Tokyo (JP)

(72) Inventors: Hirohide Nakaguma, Sakura (JP); Tetsuo Takada, Sakura (JP); Ayako Isshiki, Sakura (JP)

(73) Assignee: FUJIFILM Corporation, Tokyo (JP)

( * ) Notice: Subject to any disclaimer, the term of this patent is extended or adjusted under 35 U.S.C. 154(b) by 197 days.

(21) Appl. No.: 16/467,520

(22) PCT Filed: Dec. 12, 2017

(86) PCT No.: PCT/JP2017/044508
§ 371 (c)(1),
(2) Date: Jun. 7, 2019

(87) PCT Pub. No.: WO2018/116904
PCT Pub. Date: Jun. 28, 2018

(65) Prior Publication Data
US 2019/0338243 A1    Nov. 7, 2019

(30) Foreign Application Priority Data

Dec. 22, 2016  (JP) .............................. JP2016-248893

(51) Int. Cl.
| | | |
|---|---|---|
| *C12N 5/00* | (2006.01) |
| *C08F 299/02* | (2006.01) |
| *C12N 5/074* | (2010.01) |
| *C08F 220/38* | (2006.01) |
| *C08F 220/12* | (2006.01) |
| *C08F 220/16* | (2006.01) |
| *C08L 33/14* | (2006.01) |
| *C08L 87/00* | (2006.01) |
| *C08G 81/02* | (2006.01) |
| *C08G 81/00* | (2006.01) |

(52) U.S. Cl.
CPC .......... *C12N 5/0068* (2013.01); *C08F 220/12* (2013.01); *C08F 220/16* (2013.01); *C08F 220/387* (2020.02); *C08F 299/024* (2013.01); *C08L 33/14* (2013.01); *C08L 87/00* (2013.01); *C12N 5/0607* (2013.01); *C12N 5/0696* (2013.01); *C08G 81/00* (2013.01); *C08G 81/02* (2013.01); *C08G 81/024* (2013.01); *C12N 2533/30* (2013.01); *C12N 2533/52* (2013.01); *C12N 2533/54* (2013.01); *C12N 2533/90* (2013.01); *C12N 2539/00* (2013.01)

(58) Field of Classification Search
None
See application file for complete search history.

(56) References Cited

U.S. PATENT DOCUMENTS

| | | | |
|---|---|---|---|
| 8,664,463 B2 | 3/2014 | Zhang et al. | |
| 2011/0033928 A1 | 2/2011 | Smith et al. | |
| 2011/0183418 A1* | 7/2011 | Martin | C07K 7/08 435/396 |
| 2014/0212973 A1* | 7/2014 | Nakayama | C12N 5/0068 435/396 |
| 2016/0000824 A1 | 1/2016 | Exner et al. | |
| 2017/0029763 A1 | 2/2017 | Takada | |

FOREIGN PATENT DOCUMENTS

| | | |
|---|---|---|
| CN | 103080295 A | 5/2013 |
| CN | 103781812 A | 5/2014 |
| EP | 0470681 A2 | 2/1992 |
| EP | 0529751 A1 | 3/1993 |
| EP | 2330182 A1 | 6/2011 |
| EP | 2746308 A2 | 6/2014 |
| JP | H05-168470 A | 7/1993 |
| JP | 2007-049918 A | 3/2007 |
| JP | 2013-194084 A | 9/2013 |
| JP | 2013-195399 A | 9/2013 |
| JP | 2013195399 A * | 9/2013 |
| JP | 2014-140384 A | 8/2014 |
| WO | 2011/043405 A1 | 4/2011 |
| WO | 2014/199754 A1 | 12/2014 |
| WO | 2015/093393 A1 | 6/2015 |
| WO | 2016/199552 A1 | 12/2016 |

OTHER PUBLICATIONS

JP2013195399 English Machine Translation, prepared Jul. 9, 2021. (Year: 2021).*
A. Mellati et al., "Influence of Polymer Molecular Weight on the in Vitro Cytotoxicity of Poly (N-isopropylacrylamide)," Materials Science and Engineering C, vol. 59, 2016, pp. 509-513. (cited in the ISR).
International Search Report dated Mar. 13, 2018, issued for PCT/JP2017/044508.
Office Action dated Aug. 23, 2018, issued in the corresponding Japanese patent application No. 2018-535906 with its English Machine Translation.
Extended European Search Report dated Aug. 4, 2020, issued in the corresponding European patent application No. 17883177.2.
Office Action dated Mar. 1, 2022, issued in the corresponding Chinese patent application No. 201780079653.5 with its English Machine Translation.
Hau-Nan Lee et al., "Lower Critical Solution Temperature (LCST) Phase Behavior of Poly(ethylene oxide) in Ionic Liquids," Journal of Physical Chemistry Letters, Jul. 14, 2010, 2 pages.

(Continued)

*Primary Examiner* — Christopher M Rodd
(74) *Attorney, Agent, or Firm* — Locke Lord LLP

(57) ABSTRACT

The present invention is to provide a cell culture substrate including a block polymer including a segment having a lower critical solution temperature and a hydrophobic segment, the cell culture substrate further including an adhesive matrix, in which the adhesive matrix is an extracellular matrix and/or an adhesive synthetic matrix. Furthermore, the invention is to provide a cell culture substrate in which the extracellular matrix is at least one selected from laminin, fibronectin, vitronectin, cadherin, and fragments thereof, and/or the adhesive synthetic matrix is poly[2-(methacryloyloxy)ethyl dimethyl-(3-sulfopropyl) ammonium hydroxide] or an oligopeptide-carrying polymer.

20 Claims, No Drawings

(56) References Cited

OTHER PUBLICATIONS

Eunsong Choi et al., "Entropic Mechanism for the Lower Critical Solution Temperature of Poly(ethylene oxide) in a Room Temperature Ionic Liquid," ACS Macro Letters, vol. 4, Jul. 21, 2015, pp. 799-803.

Notification of Reason for Refusal dated Jun. 3, 2022, issued for Korean Patent Application No. 10-2019-7014082 and English translation thereof.

\* cited by examiner

CELL CULTURE SUBSTRATE

TECHNICAL FIELD

The present invention relates to a substrate for use in cell culture.

BACKGROUND ART

Human pluripotent stem cells such as human iPS cells or ES cells have attracted much attention, in view of the applicability to pathological elucidation, new drug development, and regenerative medicine. For the utilization of human pluripotent stem cells, it is necessary to culture the cells stably and safely, and it is also necessary to apply, after the cultured cells are harvested, the harvested cells to drug discovery or medical treatment.

Conventionally, low culture rates have been a problem for human pluripotent stem cells. As one of the solutions, a culturing method of utilizing feeder cells has been attempted; however, since there is a problem that feeder cells that have been used cause contamination, it cannot be said that the method is safe.

As countermeasures for that, it has been reported in PTL 1 that human pluripotent stem cells can be cultured even in a feeder cell-free manner, by coating laminin and laminin fragments, which are extracellular matrices, on a cell culture substrate.

Meanwhile, according to PTL 1, culturing on the substrate is possible; however, nothing is mentioned about the harvest of cultured cells, and there still is a problem in view of saying that cultured cells are utilized. For example, since cells cultured by the above-described method have strong adhesion to the extracellular matrices, cells are harvested by a method of enzymatically treating the cells and then physically scraping the cells with a cell scraper (spatula made of rubber or a resin) or the like. Thus, from the viewpoint that the operation efficiency is low and cells are physically stimulated, there is a problem that the method adversely affects the survival rate of cells.

On the other hand, on the occasion of utilizing the extracellular matrices such as laminin for human pluripotent stem cells, there is a problem that the extracellular matrices are likely to be deactivated. Particularly, when the substrate surface is dry, the extracellular matrices are deactivated, and the culture efficiency of human pluripotent stem cells is decreased. When storage, transportation, and the like of a cell culture substrate are considered, it is important to maintain the culture efficiency even in a dry state. In PTL 2, a cell culture substrate that is coated with proteins other than laminin and can thereby withstand a dry state, is disclosed; however, although culturing is also made possible in this way, the problem with the harvest of cultured cells is not addressed.

CITATION LIST

Patent Literature

PTL 1: WO 2011/043405
PTL 2: WO 2014/199754

SUMMARY OF INVENTION

Technical Problem

It is an object of the present invention to provide a cell culture substrate, with which even human pluripotent stem cells can be cultured with high efficiency and the cells obtained after culturing can be detached and harvested while maintaining a high survival rate. Furthermore, another object of the invention is to provide a cell culture substrate that allows cell detachment and can withstand even a dry state.

Solution to Problem

The inventors conducted a thorough investigation, and as a result, the inventors found that the problems described above can be solved by providing a cell culture substrate including a block polymer including a segment having a lower critical solution temperature and a hydrophobic segment, the cell culture substrate further including an adhesive matrix, in which the adhesive matrix is an extracellular matrix and/or an adhesive synthetic matrix.

Furthermore, there is provided a cell culture substrate in which the extracellular matrix is at least one selected from laminin, fibronectin, vitronectin, cadherin, and fragments thereof, or a cell culture substrate in which the adhesive synthetic matrix is poly[2-(methacryloyloxy)ethyl dimethyl-(3-sulfopropyl) ammonium hydroxide] or an oligopeptide-carrying polymer.

Furthermore, there is provided a cell culture substrate in which a degree of polymerization of the segment having a lower critical solution temperature is 400 to 10,000.

Furthermore, there is provided a cell culture substrate in which the hydrophobic segment is obtainable by polymerizing a monomer represented by the following Formula (1).

[Chem. 1]

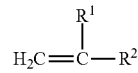

(1)

wherein in Formula (1), $R^1$ represents a hydrogen atom or a methyl group; and $R^2$ represents any one of a phenyl group, a carboxyalkyl group having an alkyl with 1 to 8 carbon atoms, a carboxyaralkyl group having an aralkyl with 7 to 8 carbon atoms, a group represented by the following Formula (2), or a group represented by the following Formula (3).

[Chem. 2]

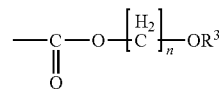

(2)

wherein in Formula (2), n represents 2 or 3; and $R^3$ represents an alkyl group having 1 to 3 carbon atoms.

[Chem. 3]

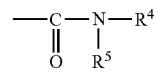

(3)

wherein in Formula (3), $R^4$ and $R^5$ each independently represent a hydrogen atom or an alkyl group having 1 to 6 carbon atoms; and the total number of carbon atoms of $R^4$ and $R^5$ is 4 or more.

Furthermore, there is provided a cell culture substrate further including at least one protein selected from gelatin, collagen, and/or albumin on the cell culture substrate.

Advantageous Effects of Invention

The cell culture substrate of the present invention allows human pluripotent stem cells to be cultured with high efficiency, and the cells obtained after culturing can be detached and harvested from the substrate with a high survival rate.

Furthermore, a substrate that enables, even after going through a dry state, cell culture and also enables cell detachment is disclosed.

DESCRIPTION OF EMBODIMENTS

The present invention is to provide a cell culture substrate including a block polymer including a segment having a lower critical solution temperature and a hydrophobic segment, the cell culture substrate further including an adhesive matrix, in which the adhesive matrix is an extracellular matrix and/or an adhesive synthetic matrix.

[Segment Having Lower Critical Solution Temperature]

The segment having a lower critical solution temperature according to the present invention is a segment for the block copolymer, and the segment refers to a segment composed of a polymer that dissolves in water when the temperatures reaches a certain temperature or lower.

The segment having a lower critical solution temperature according to the present invention is a polymer that dissolves in water when the temperature reaches a certain temperature or below as described below. Examples of the polymer having a lower critical solution temperature include the following 1) and 2).

1) A homopolymer having a lower critical solution temperature by polymerizing.

2) A copolymer of a hydrophobized monomer and a hydrophilic monomer.

The polymer 1) is a homopolymer segment by polymerizing only a monomer that gives a homopolymer having a lower critical solution temperature. Examples of the monomer that gives a homopolymer having a lower critical solution temperature include N-isopropyl (meth)acrylamide, N-n-propyl (meth)acrylamide, N-cyclopropyl (meth)acrylamide, N-ethoxyethyl (meth)acrylamide, N-tetrahydrofurfuryl (meth)acrylamide, N-ethylacrylamide, N-ethyl-N-methylacrylamide, N, N-diethylacrylamide, N-methyl-N-n-propylacrylamide, N-methyl-N-isopropylacrylamide, N-acryloylpiperidine, and N-acryloylpyrrolidine. These monomers may be utilized singly, or a plurality of kinds thereof may be utilized simultaneously.

The segment obtainable by polymerizing a monomer that gives a homopolymer having a lower critical solution temperature according to 1) can conveniently produce a polymer having a lower critical solution temperature. However, these monomers have low adhesiveness to plastic surfaces and have a problem that when brought into contact with water, a coated polymer layer is easily detachable. However, since the cell culture substrate of the present invention contains a hydrophobic segment, the cell culture substrate has excellent water resistance, and therefore, the culture substrate can be used without detachment.

2) is a copolymer of a hydrophobized monomer and a hydrophilic monomer. In order for a copolymer of a hydrophobized monomer and a hydrophilic monomer to have a lower critical solution temperature, examples include:

2-1) a case in which the hydrophilic monomer is a monomer that gives a homopolymer having a lower critical solution temperature; and 2-2) a copolymer (B1) of monomer (a) represented by the following Formula (1) and a hydrophilic amide-based vinyl monomer (b), a copolymer (B2) of the above-described or monomer (a) and monomer (c) represented by the following Formula (2), or a copolymer (B3) of monomer (a) and a polyethylene glycol chain-containing monomer (d) represented by the following Formula (3).

[Chem. 4]

wherein $R_1$ represents a hydrogen atom or a methyl group; $R_2$ represents an alkylene group having 2 or 3 carbon atoms; and $R_3$ represents an alkyl group having 1 or 2 carbon atoms.

[Chem. 5]

wherein $R_4$ represents a hydrogen atom or a methyl group; and $R_5$ represents an alkylene group having 2 or 3 carbon atoms.

[Chem. 6]

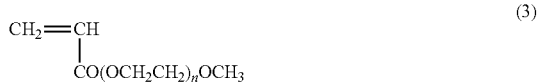

wherein n represents an integer of 2 to 20.

Examples of the hydrophilic amide-based monomer (b) include dimethylacrylamide, acrylamide, methylacrylamide, and ethylacrylamide.

A hydrophobized monomer is a monomer that is water-soluble originally but becomes insoluble in an aqueous solvent when polymerized. In a case in which such a monomer is included in a copolymer, a cell culture substrate that has excellent water resistance and is not easily detachable from the supporting medium, can be obtained.

Regarding the hydrophobized monomer, a compound represented by Formula (1), diacetone acrylamide, polypropylene glycol (meth)acrylate, methoxy diethylene glycol acrylate, and methoxy triethylene glycol acrylate may be mentioned. These may be used singly, or a plurality of kinds thereof may be used simultaneously. Among them, 2-methoxyethyl acrylate, 2-ethoxyethyl acrylate, and 3-methoxypropyl acrylate are preferred, and 2-methoxyethyl acrylate and 2-ethoxyethyl acrylate are particularly preferred.

In the case of the copolymer segment disclosed in 2-2), the lower critical solution temperature of the copolymer segment thus obtainable can be widely controlled by the types or ratio of the monomers. Furthermore, by changing the types or ratio of the monomers according to the type of cells, the copolymer segment acquires more satisfactory cell adhesiveness and proliferation properties, and cells can be cultured, which is preferable. For example, as the ratio of monomer (b or c or d) is increased with respect to monomer (a), the lower critical solution temperature of the copolymer thus obtainable is shifted toward the higher temperature side. This ratio and the lower critical solution temperature are in an almost linear relationship. Since the cell culture temperature is usually 37° C., it is preferable to prepare the copolymer such that the lower critical solution temperature of the copolymer thus obtainable is near 20° C. to 32° C.

Furthermore, the segment having a lower critical solution temperature according to the present invention can include a monomer that is not included in the group consisting of a monomer that gives a homopolymer having a lower critical solution temperature, a hydrophilic monomer, and a hydrophobized monomer, to the extent of having a lower critical solution temperature.

In regard to the block polymer according to the present invention, the degree of polymerization of the segment having a lower critical solution temperature is preferably 400 to 10,000. It is because in a case in which the degree of polymerization is 400 or higher, cell detachability is further improved, and in a case in which the degree of polymerization is lower than 10,000, synthesis of the block polymer is more feasible.

A preferred degree of polymerization is 1,000 to 8,000, and within this range, an excellent balance is achieved between cell detachability and culture efficiency. A value of 3,000 to 6,000 is particularly preferred.

[Hydrophobic Segment]

The block polymer of the present invention has a hydrophobic segment. Meanwhile, according to the present specification, the term "hydrophobicity" for a segment of the block polymer means that a polymer formed from the segment has a solubility at 25° C. in water of less than 0.5 g/100 mL. A hydrophobic segment includes at least a monomer unit of a hydrophobic monomer.

Since the block polymer of the present invention has a hydrophobic segment, even though the block polymer has a segment having a lower critical solution temperature, which causes poor water resistance, the block polymer has excellent water resistance and has excellent adhesiveness to a supporting medium.

The hydrophobic monomer is not particularly limited as long as it is a monomer that is hydrophobized after polymerization; however, preferred examples include monomers represented by the following Formulae (1) to (3). In addition, these hydrophobic monomers may be used singly, or two or more kinds thereof may be used in combination.

[Chem. 7]

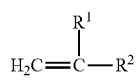

(1)

wherein in Formula (1), $R^1$ represents a hydrogen atom or a methyl group; and $R^2$ represents any one of a phenyl group, a carboxyalkyl group having an alkyl with 1 to 8 carbon atoms, a carboxyaralkyl group having an aralkyl with 7 to 8 carbon atoms, a group represented by the following Formula (2), or a group represented by the following Formula (3).

[Chem. 8]

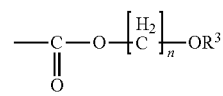

(2)

wherein in Formula (2), n represents 2 or 3; and $R^3$ represents an alkyl group having 1 to 3 carbon atoms.

[Chem. 9]

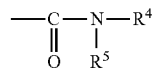

(3)

wherein in Formula (3), $R^4$ and $R^5$ each independently represent a hydrogen atom or an alkyl group having 1 to 6 carbon atoms; and the total number of carbon atoms of $R^4$ and $R^5$ is 5 or more.

Among these, as the monomer represented by Formula (1) is used, a polymer segment thus obtainable becomes hydrophobic, and the cell culture substrate acquires excellent water resistance and adhesiveness to a supporting medium, which is preferable.

Among them, preferred examples include ethyl acrylate, butyl acrylate, and styrene, and a particularly preferred example is butyl acrylate.

With regard to the block polymer of the present invention, the degree of polymerization of the hydrophobic segment is preferably 50 to 1,000. It is because in a case in which the degree of polymerization is 50 or higher, water resistance becomes more satisfactory, and in a case in which the degree of polymerization is lower than 1,000, cell detachability becomes more satisfactory.

[Block Polymer]

The block polymer of the present invention is a polymer including a segment having a lower critical solution temperature and a hydrophobic segment as described above. When the segment having a lower critical solution temperature is designated as A, and the hydrophobic segment is designated as B, the block polymer of the present invention may be a diblock type of AB or a triblock type of ABA or BAB, or may be a polymer having a larger number of segments. Preferably, the block polymer is a diblock type or triblock type polymer, and particularly preferably a diblock type polymer.

[Molecular Weight of Block Polymer]

The molecular weight of the block polymer is, as the weight average molecular weight (Mw), preferably 50,000 to 1,000,000, more preferably 70,000 to 900,000, and even more preferably 400,000 to 800,000. When the weight average molecular weight is 50,000 or more, it is preferable because the block polymer has high cell detachability, and when the weight average molecular weight is 1,000,000 or less, it is preferable because handling is easy.

[Method for Producing Block Polymer]

The method for producing the block polymer is not particularly limited, and any known method can be employed. Above all, the method is preferably precise radical polymerization; more preferably reversible addition fragmentation chain transfer (RAFT) polymerization, atom transfer radical polymerization (ATRP), or nitroxide-mediated polymerization (NMP); and even more preferably RAFT polymerization.

[Method for Forming Block Polymer]

As a preferable method for forming the cell culture substrate of the present invention, a method of coating a coating agent including the block polymer of the present invention on the above-mentioned supporting medium may be employed.

<Coating Agent>

The coating agent includes a block polymer and a solvent. In addition to those, if necessary, the coating agent may further include additives and the like.

[Block Polymer]

Regarding the block polymer, since the above-mentioned block polymer is used, further explanation will not be repeated here.

Meanwhile, only one kind of block polymer may be included, or two or more kinds of block polymers having different configurations may be included.

The content of the block polymer is preferably 0.01% to 90% by mass, and more preferably 0.1% to 50% by mass, with respect to the total mass of the coating agent. When the content of the block polymer is 0.01% by mass or more, it is preferable from the viewpoint that the coating film thus obtainable is likely to exhibit surface hydrophilicity. On the other hand, when the content of the block polymer is 90% by mass or less, since the viscosity is low, it is preferable from the viewpoint that coating suitability is enhanced.

[Solvent]

The solvent that can be included in the coating agent is not particularly limited, and any known solvent can be used.

A specific example of the solvent may be water or an organic solvent.

Examples of the organic solvent include alcohol-based solvents such as methanol, ethanol, isopropyl alcohol, butanol, sec-butanol, iso-butanol, and tert-butanol; ether-based solvents such as tetrahydrofuran and 1,4-dioxane; ketone-based solvents such as cyclohexanone and methyl isobutyl ketone; nitrile-based solvents such as acetonitrile; amide-based solvents such as dimethylformamide and dimethylacetamide; dimethyl sulfoxide; dioxirane; and pyrrolidone. Among these, as an organic solvent, it is preferable to use an alcohol-based solvent, and it is more preferable to use methanol, ethanol, propanol, isopropyl alcohol, or tert-butanol.

Among the solvents described above, it is preferable that the solvent is water or an alcohol-based solvent, and is more preferably methanol, ethanol, propanol, isopropyl alcohol, or tert-butanol.

The above-mentioned solvents may be used singly, or two or more kinds thereof may be used in combination.

The content of the solvent in the coating agent is preferably 10% to 99.99% by mass, more preferably 50% to 99.9% by mass, and even more preferably 80% to 99.5% by mass, with respect to the total mass of the coating agent. When the content of the solvent is 10% by mass or more, the viscosity of the coating agent solution becomes lower, and therefore, it is preferable from the viewpoint of having excellent coating suitability. On the other hand, when the content of the solvent is 99.99% by mass or less, the thickness of the coating film after coating does not become too thin, and thus it is preferable.

[Additives]

The coating agent may include additives according to the purpose of use.

The additives are not particularly limited, and any known additives can be used. Specific examples include an excipient, a surfactant, a plasticizer, an antifoaming agent, a pigment, an antioxidant, an antibiotic substance, an ultraviolet absorber, a crystal nucleating agent, a crystallization accelerator, a stabilizer, and an antibacterial agent. These additives may be used singly, or two or more kinds thereof may be used as mixtures.

The method of coating the coating agent is not particularly limited, and examples include a spray coating method, a flow coating method, and an immersion method.

Furthermore, in a case in which the substrate is in a tubular shape, a method of passing the coating agent liquid therethrough may be considered. At this time, after the passage of the coating agent liquid, usually, a solvent is passed through so as to remove any excess coating agent inside the tube.

The drying conditions are also not particularly limited, and the coating film may be subjected to natural drying or heated drying. The drying temperature in the case of heated drying may vary depending on the coating agent used; however, the drying temperature is preferably 30° C. to 70° C., and more preferably 40° C. to 60° C. By controlling drying, a coating film having some of the solvent remaining therein can be obtained.

[Adhesive Matrix]

Since the cell culture substrate of the present invention has an adhesive matrix within the substrate, the culturing performance for human pluripotent stem cells is enhanced. Examples of the adhesive matrix include an extracellular matrix and an adhesive synthetic matrix.

Specific examples of the extracellular matrix include laminin, fibronectin, vitronectin, cadherin, and fragments thereof. Preferred examples include laminin, vitronectin, and fragments thereof. Regarding the extracellular matrix, any animal-derived extracellular matrix can be utilized; however, human- and mouse-derived extracellular matrices are preferred. More preferred are extracellular matrices produced as recombinant proteins. As commercially available products, Matrigel (manufactured by Corning, Inc.), Geltrex (manufactured by Thermo Fisher Scientific, Inc.), iMatrix-511 (manufactured by Nippi, Inc.), Laminin 521 (BioLamina AB), and the like can be utilized.

Simultaneously with the extracellular matrix, a Rho-associated coiled-coil kinase (ROCK) inhibitor may be used. By using a ROCK Inhibitor, culture of human pluripotent stem cells dispersed into single cells is further facilitated. Examples include Y-27632 (Wako Pure Chemical Industries, Ltd.) and Fasudil hydrochloride (manufactured by Tokyo Chemical Industry Co., Ltd.).

The adhesive synthetic matrix may be poly[2-(methacryloyloxy)ethyl dimethyl-(3-sulfopropyl) ammonium hydroxide] (hereinafter, abbreviated to PMEDSAH) or an oligopeptide-carrying polymer. The oligopeptide-carrying polymer is a substrate obtained by covalently bonding an oligopeptide having an arginine-glycine-aspartic acid (RGD) sequence, which has cell adhesive activity, to a polymer. A commercially available product thereof may be Synthemax (manufactured by Corning, Inc.).

The adhesive matrix may be provided to the substrate by any method. For example, the adhesive matrix may be mixed into the substrate, or the adhesive matrix may be coated on the substrate. Furthermore, the adhesive matrix may be incorporated into a medium for cell culture and may be provided in the form of being brought into contact with the substrate together with the medium.

This adhesive matrix may exist uniformly in the substrate or may exist non-uniformly. It is preferable in a case in which the adhesive matrix exists on the substrate surface. In a case in which supply of the adhesive matrix is carried out by coating, regarding the coating method, a solution of the adhesive matrix may be applied using a conventionally known method, and the solution may be applied by spray coating, spin coating, inkjetting or the like, or may be stamped using a plate. A method of pouring the solution on the substrate, leaving the substrate to stand for a certain time period, and then removing the solution may also be used, and the application method may be selected as appropriate according to the method of use.

In the case of coating the adhesive matrix on the surface of the cell culture substrate, the coating amount is preferably 0.01 to 5 µg/cm$^2$, more preferably 0.2 to 2 µg/cm$^2$, and particularly preferably 0.5 to 1 µg/cm$^2$, per area of the cell culture substrate.

[Gelatin, Collagen, or Albumin]

Furthermore, in order to maintain the activity of the adhesive matrix or to increase the cell culture efficiency, gelatin, collagen, or albumin may be caused to exist on the cell culture substrate. Gelatin, collagen, or albumin may be mixed into the cell culture substrate or may be coated thereon, similarly to the adhesive matrix. In the case of coating the material, it is preferable that gelatin, collagen, or albumin is coated first, and then the adhesive matrix is coated, from the viewpoint of maintaining the activity of the adhesive matrix or from the viewpoint of the cell culture efficiency. Furthermore, gelatin, collagen, or albumin may be used singly, or a plurality of kinds thereof may be used simultaneously.

The coating amount of gelatin, collagen, or albumin is preferably 0.5 to 500 µg/cm$^2$, more preferably 5 to 200 µg/cm$^2$, and particularly preferably 20 to 100 µg/cm$^2$.

The cell culture substrate of the present invention may be used as a simple substance; however, from the viewpoints of convenience in transportation, storage, and the like, it is preferable that the cell culture substrate is formed on a supporting medium. Particularly preferred is a method of laminating the cell culture substrate on a supporting medium and producing a laminate.

[Other Admixtures]

The cell culture substrate of the present invention may include admixtures in addition to the block polymer, extracellular matrix, and gelatin, or collagen. For example, an antiseptic agent, an antibacterial agent, a coloring material, a fragrance, an enzyme, a sugar, a protein, a peptide, an amino acid, a cell, a DNA, a salt, a water-soluble organic solvent, a surfactant, a polymer compound, a leveling agent, and the like may also be included.

[Cell Culture Substrate]

The shape of the cell culture substrate of the present invention is not particularly limited as long as cell culture can be achieved thereon, and cultured cells can be easily detached by a low temperature treatment. Examples include a film-shaped substrate, a dish-shaped substrate, a bottle-shaped substrate, a tube-shaped substrate, a thread-shaped or rod-shaped substrate having a thickness of 5 nm to 5 mm, a bag-shaped substrate, a multi-well plate-shaped substrate, a microflow channel-shaped substrate, a porous membrane-shaped or network-shaped substrate (for example, TRANSWELL or a cell strainer), and a spherical-shaped substrate having a particle size of preferably 10 to 2,000 µm, and more preferably 100 to 500 µm.

The cell culture substrate of the present invention may be used alone as a simple substance. Preferably, the cell culture substrate is used in the form of a cell culture equipment including a supporting medium and the substrate formed on the supporting medium. It is because when the cell culture substrate is used in the form of a cell culture equipment, excellent convenience in transportation, storage, and the like is obtained, and the cell culture substrate can also be used directly as a culture container or a culture carrier.

The material of the supporting medium to be used for the present invention is not particularly limited as long as the culture substrate can be sufficiently adhered thereto, cell culture can occur on the culture substrate thus adhered, and cultured cells can be easily detached by a low temperature treatment. For example, a styrene-based resin such as polystyrene; a polyolefin-based resin such as polypropylene; a polyurethane-based resin; a polycarbonate; polyethylene terephthalate (PET); a polysulfone-based resin; a fluororesin, a polysaccharide natural polymer such as cellulose; an inorganic material such as glass or ceramic; and a metallic material such as stainless steel or titanium, are suitably used.

The shape of the supporting medium is not particularly limited, and any shape that can serve as a supporting medium of the cell culture substrate of the present invention is acceptable. Examples include a film-shaped supporting medium, a membrane-shaped supporting medium, a plate-shaped supporting medium, a spherical-shaped supporting medium, a polygonal-shaped supporting medium, a rod-shaped supporting medium, a dish-shaped supporting medium, a bottle-shaped supporting medium, a tubular-shaped supporting medium, a needle/thread-shaped supporting medium, a fiber-shaped supporting medium, a bag-shaped supporting medium, a multi-well plate-shaped supporting medium, a microflow channel-shaped supporting medium, a porous membrane-shaped supporting medium, and a network-shaped supporting medium (for example, TRANSWELL or a cell strainer). A shape combining these is acceptable, and an irregularly shaped supporting medium that does not have a particular shape is also acceptable.

Furthermore, the cell culture substrate of the present invention may be integrated with a supporting medium and used as a cell culture equipment, or the cell culture substrate may be detached from the supporting medium and used alone.

[Cultured Cells]

The cell culture substrate of the present invention enables suitable culturing of various cells, particularly animal cells. Regarding the animal cells, the origin may be any animal, and examples include human being, mouse, and monkey, while artificial cells are also acceptable. The type of cell is not particularly limited; however, examples include epithelial cells (corneal epithelial cells, and the like), endothelial cells (human umbilical vein endothelial cells, and the like), fibroblastic cells (human skin fibroblasts, mouse fibroblasts, and the like), blood corpuscles, contractile cells (skeletal muscle cells, cardiac muscle cells, and the like), blood and immune cells (red blood corpuscles, microphages, and the like), nerve cells (neurons, glial cells, and the like), pigment cells (retinal pigment cells, and the like), liver cells, cartilage cells, osteoblastic cells, and stem cells (ES cells, iPS cells, hematopoietic stem cells, skin stem cells, germ stem cells, EC cells, EG cells, and neural stem cells). Among them, the cell culture substrate of the present invention can be suitably utilized for stem cells that are difficult to culture, particularly ES cells and iPS cells.

[Dry Cell Culture Substrate]

The cell culture substrate of the present invention enables culturing of human pluripotent stem cells even in a dry state. Therefore, since the cell culture substrate can withstand long-term storage or transportation, the cell culture substrate is highly industrially applicable.

The drying method is not particularly limited, and the cell culture substrate may be laminated on the supporting medium that will be described below and then dried. For example, room temperature drying (18° C. to 30° C., humidity 20% to 60% RH), heated drying (30° C. to 37° C.), and drying using a constant temperature dryer or a desiccators may be employed. From the viewpoint of preventing denaturation of proteins, room temperature drying is preferred.

When dried, the cell culture substrate preferably has a thickness of 1,000 nm or less, and more preferably 500 nm or less. It is because when the thickness is 1,000 nm or less, satisfactory cell culturing performance is obtained.

[Method for Culturing Cells]

Regarding the culturing method, any conventionally known method may be used. For example, a predetermined amount of a medium or a culture reagent is introduced into a culture substrate formed on the bottom surface of a dish-shaped container, cells are inoculated therein, and the cells may be cultured under predetermined temperature and $CO_2$ concentration conditions, or a culture substrate formed into a filamentous form or a spherical form is introduced into a commercially available polystyrene container containing a medium, and cells may be inoculated and cultured therein. In the latter case, the cells do not adhere to the polystyrene container but adhere to the surface of the filamentous or spherical culture substrate and proliferate. For example, in a case in which a filamentous culture substrate having a thickness of 50 μm is used, since the cells grow in the longitudinal direction of a filament, the cells may be cultured in a form having a controlled cell shape. Furthermore, in the case of using a spherical culture substrate, there is an advantage that the culture substrate has a larger surface area and can culture more cells, compared to conventional dish-shaped containers.

[Method for Detaching Cells (Temperature Control Method)]

The method for detaching cultured cells from the substrate is not particularly limited; however, for example, after completion of culturing, the medium at 37° C. is replaced with a medium at a predetermined temperature (6° C. to 30° C.), the system is left to stand at a predetermined temperature (6° C. to 30° C.), and natural detachment of cells may be waited for. Alternatively, cells may be detached by physically stimulating the cells by lightly agitating the culture container, by a "pipetting" operation of sucking in and out the medium with a pipette, or with a mild water stream.

[Method for Detaching Cells (Enzymatic Method)]

In a case in which it is wished to break binding between cells and obtain individual single cells, a detachment method based on an enzymatic treatment may be used. The type of the protease to be used may be selected as appropriate according to the type of the cells. Examples include trypsin, trypsin/EDTA, and TrypLE Select (Thermo Fisher Scientific, Inc.). The treatment temperature or time may be adjusted as appropriate by the type of cells or the adhesive force to the substrate. For example, a method of removing the culture after completion of culturing, washing cells with a buffer solution or the like, adding an enzyme solution, leaving the system to stand for a certain time at 37° C., subsequently removing the enzyme solution, adding a buffer solution or a medium at a predetermined temperature (6° C. to 37° C.), and detaching the cells by standing or a "pipetting" operation, may be mentioned. Of course, the cells may also be detached by combining a low temperature treatment and the use of enzymes.

EXAMPLES

Hereinafter, the present invention will be specifically described by way of Examples; however, the scope of the present invention is not intended to be limited to these Examples.

<GPC>

The measurement method for GPC is as follows.
Apparatus: HLC-8220GPC (manufactured by Tosoh Corp.)
Solvent: N,N-dimethylformamide (DMF) solution (containing 10 mmol/L LiBr)
Column: Two TSK-gel α-M columns (manufactured by Tosoh Corp.) connected
Standard substance: PMMA standard (Shodex M-75)
(Measurement Method for NMR)
1H-NMR: JNM-ECZ400S manufactured by JEOL, Ltd.
Magnetic field strength: 400 MHz
Cumulative number: 16 times
Solvent: Deuterated methanol
Sample concentration: 10% by mass
(Measurement Method for AFM)
Atomic force microscope: NanoScope® IIIa manufactured by Bruker AXS, Inc.
Measurement mode: DFM, average of two sites of sample measurement

[Synthesis Example 1] Synthesis of Block Polymer 1

0.475 g of butyl acrylate (manufactured by Wako Pure Chemical Industries, Ltd.), 0.013 g of 2-(dodecylthiocarbonothioylthio)propanoic acid as a RAFT agent, 0.006 g of dimethyl 2,2'-azobis(2-methylpropionate), 9.0 g of t-butanol, and 1.0 g of water were subjected to sufficient nitrogen bubbling so as to remove oxygen, and then the mixture was stirred for 7 hours at 70° C. Thereby, a first reaction liquid was obtained. The conversion of butyl acrylate in this stage was 82%.

Next, a mixture of 1.68 g of N-isopropylacrylamide (hereinafter, NIPAM; manufactured by KJ Chemicals Corp.), 10.8 g of t-butanol, and 1.2 g of water was subjected to sufficient nitrogen bubbling, and then the mixture was added to the reaction liquid described above. The resultant mixture was further stirred for 20 hours at 70° C. After completion of the reaction, 22.9 g of methanol was added to the reaction liquid, and thereby an AB type temperature-responsive block polymer solution was obtained. The conversions of this block polymer were measured by NMR, and the conversion of butyl acrylate was 100%, while the conversion of NIPAM was 100%. Furthermore, the molecular weight distribution of this block polymer was measured, and the following values were obtained: Mn=41,000 and Mw=74,000. The degrees of polymerization of the hydrophobic segment and the segment having a lower critical temperature as calculated from the conversions were respectively as shown in Table 1. Furthermore, the results obtained by measuring the water-gel fraction of this block polymer by the testing method that will be described below are presented in Table 1.

[Synthesis Example 2] Synthesis of Block Polymer 2

1.19 g of butyl acrylate, 0.013 g of 2-(dodecylthiocarbonothioylthio)propanoic acid as a RAFT agent, 0.002 g of dimethyl 2,2'-azobis(2-methylpropionate), 8.0 g of t-butanol, and 1.0 g of water were subjected to sufficient nitrogen bubbling so as to remove oxygen, and then the mixture was stirred for 7 hours at 70° C. Thereby, a first reaction liquid was obtained. The conversion of butyl acrylate in this stage was 84%.

Next, a mixture of 6.3 g of NIPAM, 20.8 g of t-butanol, and 2.2 g of water was subjected to sufficient nitrogen bubbling, and then the mixture was added to the reaction liquid described above. The resultant mixture was further stirred for 20 hours at 70° C., and thereby an AB type temperature-responsive block polymer solution was obtained. The conversions of this block polymer were measured by NMR, and the conversion of butyl acrylate was 100%, while the conversion of NIPAM was 97%. Furthermore, the molecular weight distribution of this block polymer was measured, and the following values were obtained: Mn=137,000 and Mw=277,000. The degrees of polymerization of the hydrophobic segment and the segment having a lower critical temperature as calculated from the conversions were respectively as shown in Table 1. Furthermore, the results of measuring the water-gel fraction of this block polymer by the testing method described below are presented in Table 1.

[Synthesis Example 3] Synthesis of Block Polymer 3

0.474 g of butyl acrylate, 0.013 g of 2-(dodecylthiocarbonothioylthio)propanoic acid as a RAFT agent, 0.006 g of dimethyl 2,2'-azobis(2-methylpropionate), 8.0 g of t-butanol, and 1.0 g of water were subjected to sufficient nitrogen bubbling so as to remove oxygen, and then the mixture was stirred for 7 hours at 70° C. Thereby, a first reaction liquid was obtained. The conversion of butyl acrylate in this stage was 87%.

Next, a mixture of 10.5 g of NIPAM, 30.5 g of t-butanol, and 3.4 g of water was subjected to sufficient nitrogen bubbling, and then the mixture was added to the reaction liquid described above. The resultant mixture was further stirred for 20 hours at 70° C., and thereby an AB type temperature-responsive block polymer solution was obtained. The conversions of this block polymer were measured by NMR, and the conversion of butyl acrylate was 100%, while the conversion of NIPAM was 99%. Furthermore, the molecular weight distribution of this block polymer was measured, and the following values were obtained: Mn=274,000 and Mw=489,000. The degrees of polymerization of the hydrophobic segment and the segment having a lower critical temperature as calculated from the conversions were respectively as shown in Table 1. Furthermore, the results obtained by measuring the water-gel fraction of this block polymer by the testing method that will be described below are presented in Table 1.

[Synthesis Example 4] Synthesis of Block Polymer 4

0.71 g of butyl acrylate, 0.0078 g of 2-(dodecylthiocarbonothioylthio)propanoic acid as a RAFT agent, 0.0024 g of dimethyl 2,2'-azobis(2-methylpropionate), 5.4 g of t-butanol, and 0.6 g of water were subjected to sufficient nitrogen bubbling so as to remove oxygen, and then the mixture was stirred for 7 hours at 70° C. Thereby, a first reaction liquid was obtained. The conversion of butyl acrylate in this stage was 97%.

Next, a mixture of 7.55 g of NIPAM, 24.3 g of t-butanol, and 2.7 g of water was subjected to sufficient nitrogen bubbling, and then the mixture was added to the reaction liquid described above. The resultant mixture was further stirred for 20 hours at 70° C., and thereby an AB type temperature-responsive block polymer solution was obtained. The conversions of this block polymer were measured by NMR, and the conversion of butyl acrylate was 100%, while the conversion of NIPAM was 99%. Furthermore, the molecular weight distribution of this block polymer was measured, and the following values were obtained: Mn=200,000 and Mw=440,000. The degrees of polymerization of the hydrophobic segment and the segment having a lower critical temperature as calculated from the conversions were respectively as shown in Table 1. Furthermore, the results of measuring the water-gel fraction of this block polymer by the testing method that will be described below are shown in Table 1.

[Synthesis Example 5] Synthesis of Block Polymer 5

0.59 g of butyl acrylate, 0.0065 g of 2-(dodecylthiocarbonothioylthio)propanoic acid as a RAFT agent, 0.0036 g of dimethyl 2,2'-azobis(2-methylpropionate), 9.0 g of t-butanol, and 1.0 g of water were subjected to sufficient nitrogen bubbling so as to remove oxygen, and then the mixture was stirred for 7 hours at 70° C. Thereby, a first reaction liquid was obtained. The conversion of butyl acrylate in this stage was 81%.

Next, a mixture of 10.53 g of N-isopropylacrylamide (hereinafter, NIPAM; manufactured by KJ Chemicals Corp.), 49.86 g of t-butanol, and 5.54 g of water was subjected to sufficient nitrogen bubbling, and then the mixture was added to the reaction liquid described above. The resultant mixture was further stirred for 20 hours at 70° C. After completion of the reaction, 66.7 g of methanol was added to the reaction liquid, and thereby an AB type temperature-responsive block polymer solution was obtained. The conversions of this block polymer were measured by NMR, and the conversion of butyl acrylate was 100%, while the conversion of NIPAM was 99%. Furthermore, the molecular weight of this block polymer was measured, and the following values were obtained: Mn=220,000 and Mw=760,000. The degrees of polymerization of the hydrophobic segment and the segment having a lower critical temperature as calculated from the conversions were respectively as shown in Table 1. Furthermore, the results of measuring the water-gel fraction of this block polymer by the testing method that will be described below are presented in Table 1.

[Synthesis Example 6] Synthesis of Block Polymer 6

1.21 g of methoxyethyl acrylate (hereinafter, MEA; manufactured by Osaka Organic Chemical Industry, Ltd.), 0.0129 g of 2-(dodecylthiocarbonothioylthio)propanoic acid, 0.0054 g of dimethyl 2,2'-azobis(2-methylpropionate), 9.0 g of t-butanol, and 1.0 g of water were subjected to sufficient nitrogen bubbling so as to remove oxygen, and then the mixture was stirred for 7 hours at 70° C. Thereby, a first reaction liquid was obtained. The conversion of MEA in this stage was 98%.

Next, a mixture of 6.29 g of NIPAM, 18.0 g of t-butanol, and 2.0 g of water was subjected to sufficient nitrogen bubbling, and then the mixture was added to the reaction liquid described above. The resultant mixture was further stirred for 20 hours at 70° C. After completion of the reaction, 37.5 g of methanol was added to the reaction liquid, and thereby an AB type temperature-responsive block polymer solution was obtained. The conversions of this block polymer were measured by NMR, and the conversion of MEA was 100%, while the conversion of NIPAM was 98%. Furthermore, the molecular weight distribution of this block polymer was measured, and the following values were obtained: Mn=114,000 and Mw=338,000. The degrees of polymerization of the hydrophobic segment and the segment having a lower critical temperature as calculated from the conversions were respectively as shown in Table 1. Furthermore, the results obtained by measuring the water-gel fraction of this block polymer by the testing method that will be described below are presented in Table 1.

[Synthesis Example 7] Synthesis of Block Polymer 7

0.97 g of MEA, 0.0104 g of 2-(dodecylthiocarbonothioylthio)propanoic acid as a RAFT agent, 0.0032 g of dimethyl 2,2'-azobis(2-methylpropionate), 7.2 g of t-butanol, and 0.8 g of water were subjected to sufficient nitrogen bubbling so as to remove oxygen, and then the mixture was stirred for 7 hours at 70° C. Thereby, a first reaction liquid was obtained. The conversion of MEA in this stage was 92%.

Next, a mixture of 8.39 g of NIPAM, 26.5 g of t-butanol, and 2.9 g of water was subjected to sufficient nitrogen bubbling and then the mixture was added to the reaction liquid described above. The resultant mixture was further stirred for 20 hours at 70° C. After completion of the reaction, 46.8 g of methanol was added to the reaction liquid, and thereby an AB type temperature-responsive block polymer solution was obtained. The conversions of this block polymer were measured by NMR, and the conversion of MEA was 100%, while the conversion of NIPAM was 90%. Furthermore, the molecular weight distribution of this block polymer was measured, and the following values were obtained: Mn=152,000 and Mw=430,000. The degrees of polymerization of the hydrophobic segment and the segment having a lower critical temperature as calculated from the conversions were respectively as shown in Table 1. Furthermore, the results obtained by measuring the water-gel fraction of this block polymer by the testing method that will be described below are presented in Table 1.

[Synthesis Example 8] Synthesis of Block Polymer 8

1.45 g of MEA, 0.0156 g of 2-(dodecylthiocarbonothioylthio)propanoic acid as a RAFT agent, 0.008 g of dimethyl 2,2'-azobis(2-methylpropionate), 10.8 g of t-butanol, and 1.2 g of water were subjected to sufficient nitrogen bubbling so as to remove oxygen, and then the mixture was stirred for 7 hours at 70° C. Thereby, a first reaction liquid was obtained. The conversion of MEA in this stage was 98%.

Next, a mixture of 15.1 g of NIPAM, 48.8 g of t-butanol, and 5.4 g of water was subjected to sufficient nitrogen bubbling, and then the mixture was added to the reaction liquid described above. The resultant mixture was further stirred for 20 hours at 70° C. After completion of the reaction, 82.8 g of methanol was added to the reaction liquid, and thereby an AB type temperature-responsive block polymer solution was obtained. The conversions of this block polymer were measured by NMR, and the conversion of MEA was 100%, while the conversion of NIPAM was 96%. Furthermore, the molecular weight distribution of this block polymer was measured, and the following values were obtained: Mn=205,000 and Mw=576,000. The degrees of polymerization of the hydrophobic segment and the segment having a lower critical temperature as calculated from the conversions were respectively as shown in Table 1. Furthermore, the results obtained by measuring the water-gel fraction of this block polymer by the testing method that will be described below are presented in Table 1.

[Synthesis Example 9] Synthesis of Block Polymer 9

1.46 g of MEA, 0.0156 g of 2-(dodecylthiocarbonothioylthio)propanoic acid as a RAFT agent, 0.0077 g of dimethyl 2,2'-azobis(2-methylpropionate), 10.8 g of t-butanol, and 1.2 g of water were subjected to sufficient nitrogen bubbling so as to remove oxygen, and then the mixture was stirred for 7 hours at 70° C. Thereby, a first reaction liquid was obtained. The conversion of MEA in this stage was 98%.

Next, a mixture of 18.8 g of NIPAM, 58.8 g of t-butanol, and 6.4 g of water was subjected to sufficient nitrogen bubbling, and then the mixture was added to the reaction liquid described above. The resultant mixture was further stirred for 20 hours at 70° C. After completion of the reaction, 72.8 g of methanol was added to the reaction liquid, and thereby an AB type temperature-responsive block polymer solution was obtained. The conversions of this block polymer were measured by NMR, and the conversion of MEA was 100%, while the conversion of NIPAM was 97%. Furthermore, the molecular weight distribution of this block polymer was measured, and the following values were obtained: Mn=234,000 and Mw=737,000. The degrees of polymerization of the hydrophobic segment and the segment having a lower critical temperature as calculated from the conversions were respectively as shown in Table 1. Furthermore, the results obtained by measuring the water-gel fraction of this block polymer by the testing method that will be described below are presented in Table 1.

[Synthesis Example 10] Synthesis of Block Polymer 10

0.96 g of MEA, 0.0105 g of 2-(dodecylthiocarbonothioylthio)propanoic acid as a RAFT agent, 0.0049 g of dimethyl 2,2'-azobis(2-methylpropionate), 9 g of t-butanol, and 1 g of water were subjected to sufficient nitrogen bubbling so as to remove oxygen, and then the mixture was stirred for 7 hours at 70° C. Thereby, a first reaction liquid was obtained. The conversion of MEA in this stage was 97%.

Next, a mixture of 16.9 g of NIPAM, 54.7 g of t-butanol, and 6.3 g of water was subjected to sufficient nitrogen bubbling, and then the mixture was added to the reaction liquid described above. The resultant mixture was further stirred for 20 hours at 70° C. After completion of the reaction, 89 g of methanol was added to the reaction liquid, and thereby an AB type temperature-responsive block polymer solution was obtained. The conversions of this block polymer were measured by NMR, and the conversion of MEA was 100%, while the conversion of NIPAM was 98%. Furthermore, the molecular weight distribution of this block polymer was measured, and the following values were obtained: Mn=192,000 and Mw=772,000. The degrees of polymerization of the hydrophobic segment and the segment having a lower critical temperature as calculated from the conversions were respectively as shown in Table 1. Furthermore, the results obtained by measuring the water-gel fraction of this block polymer by the testing method that will be described below are presented in Table 1.

[Synthesis Example 11] Synthesis of Block Polymer 11

5.79 g of styrene (hereinafter, St; manufactured by Wako Pure Chemical Industries, Ltd.), 0.040 g of 2-(dodecylthio-carbonothioylthio)propanoic acid as a RAFT agent, and 0.0122 g of dimethyl 2,2'-azobis(2-methylpropionate) were subjected to sufficient nitrogen bubbling so as to remove oxygen, and then the mixture was stirred for 7 hours at 70° C. Thereby, a first reaction liquid was obtained. The conversion of St in this stage was 40%, and the degree of polymerization thus calculated was 200.

Next, the RAFT agent-containing polystyrene thus obtained was reprecipitated in diisopropyl ether and then was dried in a vacuum at 70° C., and thereby monomers were removed. Subsequently, a mixture of 1 g of the RAFT agent-containing polystyrene, 8.02 g of NIPAM, 45.2 of ethyl acetate, and 0.0122 g of dimethyl 2,2'-azobis(2-methylpropionate) was subjected to sufficient nitrogen bubbling, and then the mixture was added to the reaction liquid described above. The resultant mixture was further stirred for 20 hours at 70° C., and thereby an AB type temperature-responsive block polymer solution was obtained. The conversions of this block polymer were measured by NMR, and the conversion of NIPAM was 98%. Furthermore, the molecular weight distribution of this block polymer was measured, and the following values were obtained: Mn=62,000 and Mw=221,000. The degrees of the hydrophobic segment and the segment having a lower critical temperature as calculated from the conversions were respectively as shown in Table 1. Furthermore, the results obtained by measuring the water-gel fraction of this block polymer by the testing method that will be described below are presented in Table 1.

[Preparation Example 1] Synthesis of Tetrabranched RAFT Agent

According to Non Patent Literature "Macromolecules, 36, 1505 (2003)", RAFT agent "pentaerythritol tetrakis(3-1S-(1-methoxycarbonyl)ethyl trithiocarbonyl propionate)" was synthesized by the following procedure.

10 mL of dichloromethane, 1.22 g of pentaerythritol (3-mercaptopropionate), 2.00 g of carbon disulfide, and 2.04 g of triethylamine were introduced, and the mixture was stirred for one hour. Next, 1.94 g of methyl 2-bromopropionate was introduced therein, and the mixture was further stirred for 5 hours and then was washed with a 5% aqueous solution of $KHSO_4$. The mixture was further washed with water and then was dried with saturated brine. The residue was treated with magnesium sulfate, and then dichloromethane was removed using an evaporator. An orange-colored oily product thus obtained was purified by silica gel column chromatography using hexane/acetone as an eluent, and thus RAFT agent "pentaerythritol tetrakis(3-1S-(1-methoxycarbonyl)ethyl trithiocarbonyl propionate)" was obtained.

[Synthesis Example 12] Synthesis of Block Polymer 12

1.48 g of MEA, 0.013 g of pentaerythritol tetrakis(3-1S-(1-methoxycarbonyl)ethyl trithiocarbonyl propionate) as a RAFT agent, 0.0042 g of dimethyl 2,2'-azobis(2-methylproionate), 7.2 g of t-butanol, and 0.8 g of water were subjected to sufficient nitrogen bubbling so as to remove oxygen, and then the mixture was stirred for 7 hours at 70° C. Thus, a first reaction liquid was obtained. The conversion of MEA in this stage was 97%.

Next, a mixture of 12.9 g of NIPAM, 45.7 g of t-butanol, and 5 g of water was subjected to sufficient nitrogen bubbling, and then the mixture was added to the reaction liquid described above. The resultant mixture was further stirred for 20 hours at 70° C. After completion of the reaction, 60 g of methanol was added to the reaction liquid, and thereby an AB type temperature-responsive block polymer solution was obtained. The conversions of this block polymer were measured by NMR, and the conversion of MEA was 100%, while the conversion of NIPAM was 98%. Furthermore, the molecular weight distribution of this block polymer was measured, and the following values were obtained: Mn=250,000 and Mw=782,000. The degrees of polymerization of the hydrophobic segment and the segment having a lower critical temperature as calculated from the conversions were respectively as shown in Table 1. Furthermore, the results obtained by measuring the water-gel fraction of this block polymer by the testing method that will be described below are presented in Table 1.

[Synthesis Example 13] Synthesis of Block Polymer 13

1.92 g of butyl methacrylate (hereinafter, BMA; product of Wako Pure Chemical Industries, Ltd.), 0.060 g of 2-(do-decylthiocarbonothioylthio)propanoic acid as a RAFT agent, 0.012 g of dimethyl 2,2'-azobis(2-methylpropionate), 10.8 g of t-butanol, and 1.2 g of water were subjected to sufficient nitrogen bubbling so as to remove oxygen, and then the mixture was stirred for 7 hours at 70° C. Thereby, a first reaction liquid was obtained. The conversion of BMA in this stage was 83%.

Next, a mixture of 6.1 g of NIPAM, 18 g of t-butanol, and 2 g of water was subjected to sufficient nitrogen bubbling, and then the mixture was added to the reaction liquid described above. The resultant mixture was further stirred for 20 hours at 70° C., and thereby an AB type temperature-responsive block polymer solution was obtained. The conversions of this block polymer were measured by NMR, and the conversion of MEA was 100%, while the conversion of NIPAM was 99%. Furthermore, the molecular weight distribution of this block polymer was measured, and the following values were obtained: Mn=34,000 and Mw=51,000. The degrees of polymerization of the hydrophobic segment and the segment having a lower critical temperature as calculated from the conversions were respectively as shown in Table 1. Furthermore, the results obtained by measuring the water-gel fraction of this block polymer by the testing method that will be described below are presented in Table 1.

Production Example of Culture Substrate

Example 1

Block polymer 1 was diluted with methanol, thereby a 0.5% solution was produced, and 60 ul of the solution was introduced into a 35-mm Petri dish made of polystyrene (35 mm/Tissue Culture Dish, manufactured by AGC Techno Glass Co., Ltd.). Subsequently, the block polymer was washed by repeating three times an operation of drying solution at 80° C. for 30 minutes and then immersing the dried product in pure water for 10 minutes, and the block polymer was dried overnight at 40° C. Thus, a cell culture container 1 having a cell culture substrate laminated thereon was obtained. The thickness of the cell culture substrate thus obtained was measured with an atomic force microscope, and the thickness was 50 nm.

This cell culture substrate was subjected to laminin coating by the method that will be described below, and the results of performing evaluations of the iPS cell culturing performance and the temperature-sensitive detachability of cells by the testing methods that will be described below are presented in Table 1.

Examples 2 to 13

Cell culture containers 2 to 13 each having a cell culture substrate laminated thereon were produced from block polymers 2 to 13 by a method similar to that of Example 1. These cell culture substrata were subjected to laminin coating by the method that will be described below, and the results of performing evaluations of the iPS cell culturing performance and the temperature-sensitive detachability of cells by the testing methods that will be described below are presented in Table 1.

Comparative Example 1

A 35-mm Petri dish of a commercially available temperature-sensitive detaching culture container "UPCELL (polyisopropyl acrylamide homopolymer-immobilized cell culture substrate, product of Cellseed, Inc.)" was subjected to laminin coating using the laminin coating method that will be described below, and then evaluations of the iPS cell culturing performance and the iPS cell temperature-sensitive detachability were carried out by the testing methods that will be described below.

Comparative Example 2

A 35-mm Petri dish made of polystyrene of a commercially available cell culture container (TCPS, 35 mm/Tissue Culture Dish, manufactured by AGC Techno Glass Co., Ltd.) was subjected to laminin coating using the laminin coating method that will be described below, and then evaluations of the iPS cell culturing performance and the iPS cell temperature-sensitive detachability were carried out by the testing methods that will be described below.

[Laminin Coating Method of Examples 1 to 13 and Comparative Examples 1 and 2]

500 μL (equivalent to a coating amount of 0.5 μg/cm$^2$) of an aqueous solution of laminin (trade name: iMatrix, manufactured by Nippi, Inc.) having a concentration of 10 ug/mL was introduced into each of the cell culture containers of Examples 1 to 13 and Comparative Examples 1 and 2, and the cell culture containers were left to stand for 1 hour at 37° C. Subsequently, the iPS cell culture and temperature-sensitive detachment test that will be described below was performed without drying the cell culture containers.

(Water-Gel Fraction)

0.1 g of each of the dried culture substrate was wrapped with a 200-mesh stainless steel wire gauze, and the dried culture substrate was left to stand in water at 4° C. for 20 hours. Samples obtained before and after the standing were dried for 2 hours in a hot air dryer at 130° C., and the dried weights were respectively measured. Thus, the weight reduction ratio obtained before and after the standing in cold water was investigated. As this value is higher, it can be said that the culture substrate has high water resistance, and elution by water from the culture substrate does not easily occur.

[Culture of iPS Cells and Evaluation of Detachment Rate]

2 ml of StemFit Ak02N medium (manufactured by Ajinomoto Co., Inc.), to which ROCK inhibitor Y27632 (amount of addition 0.5 μg/mL of medium) had been added thereto, was added to culture container 1, and a certain amount (about 1×10$^4$ cells/cm$^2$) of human iPS cells (strain 201B7, manufactured by iPS Academia Japan, Inc.) were introduced into the culture container. The cells were left to stand in a thermostat at 37° C. in a 5% CO$_2$ atmosphere, and culture was carried out for 5 days. The medium was exchanged at a frequency of once in two days. Next, the cells were detached by a temperature control detachment method. That is, medium exchange was carried out with a cold medium at 4° C., and the cells were left to stand for 10 minutes at room temperature. Subsequently, a "pipetting operation" of sucking in and out the medium with a pipette was performed about 10 times, and thereby cell detachment was carried out. Next, the number of detached cells, the number of dead cells among the detached cells, and the total number of cultured cells were counted according to the method of "Detachment rate and survival rate of cells, and measurement of culturing performance", and the detachment rate, survival rate, and culturing performance were calculated by Formulae (6), (7), and (8).

(Detachment Rate and Survival Rate of Cells, and Measurement of Culturing Performance)

After completion of culture, a cell detachment operation is carried out by a temperature control method or an enzymatic method, and a suspension of the detached cells is suctioned into a cassette for exclusive use in cell measurement. The number of dead cells among the detached cells in the cell suspension is counted using a cell counting apparatus, NC-100 (manufactured by M&S TechnoSystems, Inc.). Furthermore, 100 μl of the detached cells is transferred into each medium in a 1.5-ml tube, and 100 μl each of Reagent A and Reagent B (manufactured by M&S TechnoSystems, Inc.) are added thereto. The mixture is uniformly mixed up by pipetting several times, and then similarly, the liquid is suctioned into a new cassette and is mounted in a cell counting apparatus, NC-100. Thus, the number of detached cells is counted. Furthermore, an appropriate amount of Reagent A is added to the Petri dish, from which all of detached cells after the detachment operation have been removed, and the Petri dish is left to stand for 10 minutes at room temperature (25° C.). Any cells remaining in the Petri dish and undetached cells are completely detached and dissolved and scraped using a scraper (rubber spatula), and then an appropriate amount of Reagent B is added thereto. The mixture is uniformly mixed up by pipetting several times and is mounted in a cell counting apparatus, NC-100. The number of undetached cells remaining in the Petri dish is counted. The cell detachment rate and survival rate, and culturing performance are calculated by the following Formulae (6), (7), and (8), respectively.

$$\text{Detachment rate}=[\text{Number of detached cells}/(\text{number of detached cells}+\text{number of undetached cells})]\times 100 \quad (6)$$

$$\text{Survival rate}=(1-\text{number of dead cells among detached cells}/\text{number of detached cells})\times 100 \quad (7)$$

$$\text{Culturing performance}=\text{Total number of cells obtained with culture substrate/total number of cells obtained with TCPS (commercially available Petri dish for tissue culture)}* \quad (8)$$

* Total number of cells=Number of detached cells+number of undetached cells (Example of Alkaline Phosphatase Staining (AP Staining))

Since undifferentiated iPS cells exhibit high alkaline phosphatase activity, they are stained dark. In contrast, differentiated cells do not exhibit alkaline phosphatase activity and are not stained.

As a reagent, "Leukocyte Alkaline Phosphatase Kit" manufactured by Sigma-Aldrich Corp. was used. Regarding the operation procedure, after completion of culture, the medium in the Petri dish is removed, a phosphate buffer solution is added thereto, cells are washed, and then the phosphate buffer solution is removed. Next, a fixing solution is added thereto, the system is left to stand for about one minute, and then the fixing solution is removed. The cells are washed with water, subsequently a stain solution is added thereto, and the mixture is left to stand for one hour at room temperature (25° C.). The stain solution is removed, the cells are washed with water, amounting agent is introduced, and the cells are covered with a cover glass and are observed with a microscope. In a case in which the cells exhibit alkaline phosphatase activity (positive), the cells are stained red.

factured by Nippi, Inc.) at a concentration of 10 μg/mL was introduced into cell culture containers 14, 26, and 28, the cell culture containers were left to stand for one hour at 37° C., subsequently the aqueous solution was discarded, and the cell culture containers were left to stand for one day at room temperature of 25° C. (relative humidity 35% to 55% RH) to be dried.

[Laminin Coating] of Example 15

500 μL (equivalent to a coating amount of 0.5 μg/cm$^2$) of an aqueous solution of laminin (trade name: iMatrix, manufactured by Nippi, Inc.) at a concentration of 10 μg/mL was introduced into cell culture container 15, the cell culture container was left to stand for one hour at 37° C., subsequently the aqueous solution was discarded, and the cell culture container was left to stand for one day at room temperature of 25° C. (relative humidity 35% to 55% RH) to be dried. Subsequently, the cell culture container was left to stand for 30 days at room temperature (25° C., 40% RH).

[Laminin Coating] of Examples 27 and 29

500 μL (equivalent to a coating amount of 0.5 μg/cm$^2$) of an aqueous solution of laminin (trade name: iMatrix, manufactured by Nippi, Inc.) at a concentration of 10 μg/mL was

TABLE 1

| | Degree of polymerization of segment | | | Cell culture | |
|---|---|---|---|---|---|
| | Hydrophobic segment | Segment having lower critical solution temperature | Water-gel fraction (%) | Cell detachment rate (4° C., %) | Culturing performance (with respect to polystyrene Petri dish) |
| Example 1 | 82 | 418 | 95 | 60 | 1.0 |
| Example 2 | 210 | 1542 | 87 | 91 | 1.0 |
| Example 3 | 87 | 2515 | 89 | 92 | 1.0 |
| Example 4 | 241 | 3006 | 93 | 93 | 1.0 |
| Example 5 | 201 | 5052 | 93 | 95 | 1.0 |
| Example 6 | 248 | 1516 | 25 | 91 | 1.0 |
| Example 7 | 231 | 2520 | 30 | 92 | 1.0 |
| Example 8 | 245 | 3004 | 45 | 93 | 1.0 |
| Example 9 | 247 | 3739 | 50 | 94 | 1.0 |
| Example 10 | 239 | 4994 | 54 | 95 | 1.0 |
| Example 11 | 195 | 1501 | 85 | 91 | 1.0 |
| Example 12 | 241 | 625 | 40 | 90 | 1.0 |
| Example 13 | 65 | 328 | 1 | 50 | 1.0 |
| Comparative Example 1 | — | — | — | 45 | 1.0 |
| Comparative Example 2 | — | — | — | 5 | 1.0 |

<Storage Stability Test>

The culture substrata of Examples 14 to 29 were all produced by the following method.

An appropriate amount of a 1 mass % methanol solution of block polymer 12 (block polymer 8 for Examples 26 and 27, and block polymer 13 for Examples 28 and 29) was introduced into a 35-mm Petri dish made of polystyrene (35 mm/Tissue Culture Dish, manufactured by AGC Techno Glass Co., Ltd.), and the solution was thinly coated on the surface of the Petri dish using a spin coater. The Petri dish was dried for 20 minutes in a thermostat at 80° C. Next, the Petri dish was washed with sterilized water, and then the Petri dish was dried for 5 hours at 40° C. in a sterile bag. Thus, cell culture containers 14 to 29 were obtained. The thickness of the coating film was measured using an AFM (atomic force microscope), and the thickness was about 20 nm.

[Laminin Coating] of Examples 14, 26, and 28

500 μL (equivalent to a coating amount of 0.5 μg/cm$^2$) of an aqueous solution of laminin (trade name: iMatrix, manuintroduced into cell culture containers 27 and 29, the cell culture containers were left to stand for one hour at 37° C., subsequently the aqueous solution was discarded, and the cell culture containers were left to stand for one day at room temperature of 25° C. (relative humidity 35% to 55% RH) to be dried. Subsequently, the cell culture containers were left to stand for 6 days at room temperature (25° C., 40% RH).

[Coating of Laminin/Gelatin Mixed Solution] of Example 16

500 μL (equivalent to a gelatin coating amount of 10 μg/cm$^2$, equivalent to a laminin coating amount of 0.5 μg/cm$^2$) of an aqueous solution including gelatin (manufactured by Nitta Gelatin, Inc.) at a concentration of 0.2 mg/ml and laminin at a concentration of 10 μg/mL was introduced into cell culture container 16, the cell culture container was left to stand for one hour at 37° C., subsequently the aqueous solution was discarded, and the cell culture container was dried for one day at room temperature of 25° C. (relative humidity 35% to 55% RH).

[Coating of Laminin/Gelatin Mixture] of Example 17

500 μL (equivalent to a gelatin coating amount of 150 μg/cm², equivalent to a laminin coating amount of 0.5 μg/cm²) of an aqueous solution including gelatin (manufactured by Nitta Gelatin, Inc.) at a concentration of 3 mg/ml and laminin at a concentration of 10 μg/mL was introduced into cell culture container 16, the cell culture container was left to stand for one hour at 37° C., subsequently the aqueous solution was discarded, and the cell culture container was dried for one day at room temperature of 25° C. (relative humidity 35% to 55% RH).

[Coating of Laminin/Gelatin Mixture] of Example 18

500 μL (equivalent to a gelatin coating amount of 150 μg/cm², equivalent to a laminin coating amount of 0.5 μg/cm²) of an aqueous solution including gelatin (manufactured by Nitta Gelatin, Inc.) at a concentration of 3 mg/ml and laminin at a concentration of 1 μg/mL was introduced into cell culture container 16, the cell culture container was left to stand for one hour at 37° C., subsequently the aqueous solution was discarded, and the cell culture container was dried for one day at room temperature of 25° C. (relative humidity 35% to 55% RH). Subsequently, the cell culture container was further left to stand for 30 days at room temperature (25° C., 40% RH).

[Coating of Collagen and Laminin] of Example 19

500 μL (equivalent to a coating amount of 5 μg/cm²) of an aqueous solution of collagen (trade name: Cellmatrix Type I-C, manufactured by Nitta Gelatin, Inc.) at a concentration of 0.1 mg/ml was introduced into cell culture container 19, the cell culture container was left to stand for one hour at 37° C., and then the aqueous solution was discarded. Subsequently, 500 μL (equivalent to a coating amount of 0.5 μg/cm²) of an aqueous solution of laminin (trade name: iMatrix, manufactured by Nippi, Inc.) at a concentration of 10 μg/mL was introduced, the cell culture container was left to stand for one hour at 37° C., subsequently the aqueous solution was discarded, and the cell culture container was dried for one day at room temperature of 25° C. (relative humidity 35% to 55% RH).

[Coating of Collagen and Laminin] of Example 20

Coating of collagen and laminin was carried out in the same manner as in Example 19, except that an aqueous solution of collagen at a concentration of 1 mg/ml was used instead of the aqueous solution of collagen at a concentration of 0.1 mg/ml of Example 19.

[Coating of Collagen and Laminin] of Example 21

Coating of collagen and laminin was carried out in the same manner as in Example 19, except that an aqueous solution of collagen at a concentration of 2 mg/ml was used instead of the aqueous solution of collagen at a concentration of 0.1 mg/ml of Example 19.

[Coating of Collagen and Laminin] of Example 22

Coating of collagen and laminin was carried out in the same manner as in Example 19, except that an aqueous solution of collagen at a concentration of 4 mg/ml was used instead of the aqueous solution of collagen at a concentration of 0.1 mg/ml of Example 19.

[Coating of Collagen and Laminin] of Example 23

Coating of collagen and laminin was carried out in the same manner as in Example 19, except that an aqueous solution of collagen at a concentration of 10 mg/ml was used instead of the aqueous solution of collagen at a concentration of 0.1 mg/ml of Example 19.

[Coating of Collagen and Laminin] of Example 24

500 μL (equivalent to a coating amount of 50 μg/cm²) of an aqueous solution of collagen (trade name: Cellmatrix Type I-C, manufactured by Nitta Gelatin, Inc.) at a concentration of 1 mg/ml was introduced into cell culture container 24, the cell culture container was left to stand for one hour at 37° C., and then the aqueous solution was discarded. Subsequently, 500 μL (equivalent to a coating amount of 0.7 μg/cm²) of an aqueous solution of laminin (trade name: iMatrix, manufactured by Nippi, Inc.) at a concentration of 14 μg/mL was introduced, the cell culture container was left to stand for one hour at 37° C., subsequently the aqueous solution was discarded, and the cell culture container was dried for one day at room temperature of 25° C. (relative humidity 35% to 55% RH).

[Coating of Collagen and Laminin] of Example 25

Coating of collagen and laminin was carried out in the same manner as in Example 24, except that an aqueous solution of laminin at a concentration of 20 μg/mL was used instead of the "aqueous solution of laminin at a concentration of 14 μg/mL" of Example 24.

Comparative Example 3

500 μL (equivalent to a coating amount of 0.5 μg/cm²) of an aqueous solution of laminin (trade name: iMatrix, manufactured by Nippi, Inc.) at a concentration of 10 μg/mL was introduced into a 35-mm Petri dish of a 35-mm Petri dish made of polystyrene (TCPS, 35 mm/Tissue Culture Dish, manufactured by AGC Techno Glass Co., Ltd.) of a commercially available cell culture container, the cell culture container was left to stand for one hour at 37° C., the aqueous solution was discarded, and the cell culture container was left to stand for one day at room temperature of 25° C. (relative humidity 35% to 55% RH) to be dried.

Comparative Example 4

500 μL (equivalent to a coating amount of 0.5 μg/cm²) of an aqueous solution of laminin (trade name: iMatrix, manufactured by Nippi, Inc.) at a concentration of 10 μg/mL was introduced into a 35-mm Petri dish of a 35-mm Petri dish made of polystyrene (TCPS, 35 mm/Tissue Culture Dish, manufactured by AGC Techno Glass Co., Ltd.) of a commercially available cell culture container, the cell culture container was left to stand for one hour at 37° C., the aqueous solution was discarded, and the cell culture container was left to stand for one day at room temperature of 25° C. (relative humidity 35% to 55% RH) to be dried. Subsequently, the cell culture container was further left to stand for 6 days at room temperature (25° C., 40% RH).

TABLE 2

|  | Example 14 | Example 15 | Example 16 | Example 17 | Example 18 | Example 19 | Example 20 | Example 21 | Example 22 | Example 23 |
|---|---|---|---|---|---|---|---|---|---|---|
| Block polymer | Block polymer 12 | Block polymer 12 | Block polymer 12 | Block polymer 12 | Block polymer 12 | Block polymer 12 | Block polymer 12 | Block polymer 12 | Block polymer 12 | Block polymer 12 |

TABLE 2-continued

|  | Example 14 | Example 15 | Example 16 | Example 17 | Example 18 | Example 19 | Example 20 | Example 21 | Example 22 | Example 23 |
|---|---|---|---|---|---|---|---|---|---|---|
| Coating amount of laminin ($\mu g/cm^2$) | 0.5 | 0.5 | 0.5 | 0.5 | 0.5 | 0.5 | 0.5 | 0.5 | 0.5 | 0.5 |
| Coating amount of gelatin ($\mu g/cm^2$) | 0 | 0 | 10 | 150 | 150 | 0 | 0 | 0 | 0 | 0 |
| Coating amount of collagen ($\mu g/cm^2$) | 0 | 0 | 0 | 0 | 0 | 5 | 50 | 100 | 200 | 500 |
| Number of days passed after drying of protein coating | 1 | 30 | 1 | 1 | 30 | 1 | 1 | 1 | 1 | 1 |
| Cell detachment rate (enzyme, %) | 95 |  | 100 | 100 |  | 94 | 100 | 100 | 100 | 100 |
| Cell detachment rate (4° C., %) | 90 | 87 | 100 | 100 | 100 | 91 | 100 | 100 | 100 | 100 |
| Culturing performance (with respect to TCPS) | 1.0 | 1.0 | 1.0 | 1.0 | 1.0 | 1.0 | 0.8 | 0.9 | 0.8 | 0.8 |
| Survival rate of harvested cells (%) | 87 |  | 90 | 90 |  | 85 | 89 | 86 | 85 | 89 |
| Maintaining undifferentiated state (AP staining) | ○ | ⊙ | ⊙ |  |  | ○ | ○ | ○ | ○ | ○ |

TABLE 3

|  | Example 24 | Example 25 | Example 26 | Example 27 | Example 28 | Example 29 | Comparative Example 3 | Comparative Example 4 |
|---|---|---|---|---|---|---|---|---|
| Block polymer | Block polymer 12 | Block polymer 12 | Block polymer 8 | Block polymer 8 | Block polymer 13 | Block polymer 13 | — | — |
| Coating amount of laminin ($\mu g/cm^2$) | 0.7 | 1 | 0.5 | 0.5 | 0.5 | 0.5 | 0.5 | 0.5 |
| Coating amount of gelatin ($\mu g/cm^2$) | 0 | 0 | 0 | 0 | 0 | 0 | 0 | 0 |
| Coating amount of collagen ($\mu g/cm^2$) | 50 | 50 | 0 | 0 | 0 | 0 | 0 | 0 |
| Number of days passed after drying of protein coating | 1 | 1 | 1 | 6 | 1 | 6 | 1 | 6 |
| Cell detachment rate (enzyme, %) | 100 | 100 | 100 | 100 | 85 | 85 | 50 | 40 |
| Cell detachment rate (4° C., %) | 100 | 100 | 91 | 93 | 50 | 50 | 7 | 5 |
| Culturing performance (with respect to TCPS) | 1.0 | 1.0 | 1.0 | 0.8 | 1.0 | 1.0 | 1.0 | 1.0 |
| Survival rate of harvested cells (%) | 93 | 92 |  |  |  |  |  |  |
| Maintaining undifferentiated state (AP staining) | ⊙ | ⊙ |  |  |  |  |  |  |

Example 30

Block polymer 10 was diluted with methanol, and a 0.12% solution was produced. 40 ul of the solution was introduced into a 35-mm Petri dish made of polystyrene (35 mm/Tissue Culture Dish, manufactured by Iwaki Cell Biology Corp.), and then the solution was left to stand for 2 hours at room temperature to be dried. The Petri dish was further rinsed respectively with ultrapure water and sterilized water, and the Petri dish was dried overnight at 40° C. Thereby, a cell culture container 30 having a cell culture substrate laminated thereon was obtained. The thickness of the cell culture substrate thus obtained was measured by spectral ellipsometry, and the thickness was 35 nm.

[Culture of iPS Cells, Evaluation of Detachment Rate]

1.5 mL of a medium (StemFit Ak02N, manufactured by Ajinomoto Co., Inc.) to which 4.8 ul of an aqueous solution of laminin (trade name: iMatrix, manufactured by Nippi, Inc.) at a concentration of 0.5 ug/ul, 1.5 ul of ROCK inhibitor Y27632 at a concentration of 3.4 ug/ul, and $1.3 \times 10^4$ cells of iPS cells (strain 201B7, manufactured by iPS Academia Japan, Inc.) had been added, was introduced into culture container 30, and the medium was left to stand in a thermostat at 37° C. in a 5% $CO_2$ atmosphere. Thus, culture was carried out for 8 days. From the third day after the day of initiating culture, the medium was exchanged everyday for consecutive 5 days.

Next, medium exchange was carried out with a cold medium at 4° C., the system was left to stand for 10 minutes at room temperature, and then a "pipetting operation" of sucking in and out the medium with a pipette was performed about 10 times. Thus, cell detachment was carried out. The cell culturing performance determined according to the above-described methods of "Detachment rate and survival rate of cells, and measurement of culturing performance" was 1.0 (equivalent to TCPS), the cell detachment rate was 95%, and the survival rate of the harvested cells was 75%.

Comparative Example 5

Evaluation of the culture of iPS cells and the detachment rate was performed in the same manner as in Example 30, except that a 35-mm Petri dish made of polystyrene (35 mm/Tissue Culture Dish, manufactured by Iwaki Cell Biology Corp.) was used. As a result, evaluation of the culture of iPS cells and the detachment rate was performed. As a result, the cell culturing performance was 1.0, the cell detachment rate was 5%, and the survival rate of the harvested cells was 20%.

INDUSTRIAL APPLICABILITY

The cell culture substrate of the present invention is to provide a cell culture substrate that allows even human pluripotent stem cells to be cultured with high efficiency and enables detachment and harvest of cells after culturing while maintaining a high survival rate. Furthermore, in addition, it is to provide a cell culture substrate that allows cell detachment and can withstand a dry state.

The invention claimed is:

1. A cell culture substrate comprising a block polymer comprising a segment having a lower critical solution temperature and a hydrophobic segment, the cell culture substrate further including an adhesive matrix,
   wherein a degree of polymerization of the segment having a lower critical solution temperature is 400 to 10,000, and
   wherein the adhesive matrix is an extracellular matrix and/or an adhesive synthetic matrix.

2. The cell culture substrate according to claim 1, wherein the extracellular matrix is at least one selected from laminin, fibronectin, vitronectin, cadherin, and fragments thereof.

3. The cell culture substrate according to claim 1, wherein the adhesive synthetic matrix is poly[2-(methacryloyloxy)ethyl dimethyl-(3-sulfopropyl) ammonium hydroxide] or an oligopeptide-carrying polymer.

4. The cell culture substrate according to claim 1, wherein the hydrophobic segment is obtainable by polymerizing a monomer represented by the following Formula (1):

[Chem. 1]

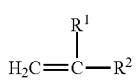

(1)

wherein in Formula (1), $R^1$ represents a hydrogen atom or a methyl group; and $R^2$ represents any one of a phenyl group, a carboxyalkyl group having an alkyl with 1 to 8 carbon atoms, a carboxyaralkyl group having an aralkyl with 7 or 8 carbon atoms, a group represented by the following Formula (2), or a group represented by the following Formula (3):

[Chem. 2]

(2)

wherein in Formula (2), n represents 2 or 3; and $R^3$ represents an alkyl group having 1 to 3 carbon atoms,

[Chem. 3]

(3)

wherein in Formula (3), $R^4$ and $R^5$ each independently represent a hydrogen atom or an alkyl group having 1 to 6 carbon atoms; and the total number of carbon atoms of $R^4$ and $R^5$ is 5 or more.

5. The cell culture substrate according to claim 1, further comprising at least one protein selected from gelatin, collagen, and/or albumin on the cell culture substrate.

6. The cell culture substrate according to claim 5, wherein the block polymer, at least one protein selected from gelatin, collagen, and/or albumin, and the adhesive matrix are sequentially laminated.

7. The cell culture substrate according to claim 1, which is a dry cell culture substrate.

8. The cell culture substrate according to claim 1, which is laminated on a supporting medium.

9. The cell culture substrate according to claim 8, which has an average thickness of 1,000 nm or less.

10. A method for producing a dry cell culture substrate, the method comprising:
    a step of coating a solution including at least one protein selected from gelatin, collagen, and/or albumin on the block polymer according to claim 1;
    a step of further coating a solution including the adhesive matrix according to claim 1 thereon to obtain a cell culture substrate; and
    a step of drying the obtained cell culture substrate.

11. A cell culture equipment comprising a supporting medium and the cell culture substrate according to claim 1.

12. The cell culture substrate according to claim 2, wherein the adhesive synthetic matrix is poly[2-(methacryloyloxy)ethyl dimethyl-(3-sulfopropyl) ammonium hydroxide] or an oligopeptide-carrying polymer.

13. The cell culture substrate according to claim 2, wherein the hydrophobic segment is obtainable by polymerizing a monomer represented by the following Formula (1):

[Chem. 1]

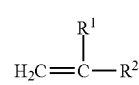

(1)

wherein in Formula (1), $R^1$ represents a hydrogen atom or a methyl group; and $R^2$ represents any one of a phenyl group, a carboxyalkyl group having an alkyl with 1 to 8 carbon atoms, a carboxyaralkyl group having an aralkyl with 7 or 8 carbon atoms, a group represented by the following Formula (2), or a group represented by the following Formula (3):

[Chem. 2]

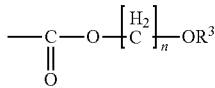

(2)

wherein in Formula (2), n represents 2 or 3; and $R^3$ represents an alkyl group having 1 to 3 carbon atoms,

[Chem. 3]

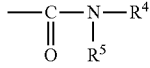

(3)

wherein in Formula (3), $R^4$ and $R^5$ each independently represent a hydrogen atom or an alkyl group having 1 to 6 carbon atoms; and the total number of carbon atoms of $R^4$ and $R^5$ is 5 or more.

14. The cell culture substrate according to claim 2, further comprising at least one protein selected from gelatin, collagen, and/or albumin on the cell culture substrate.

15. The cell culture substrate according to claim 2, which is a dry cell culture substrate.

16. The cell culture substrate according to claim 2, which is laminated on a supporting medium.

17. A cell culture equipment comprising a supporting medium and the cell culture substrate according to claim 2.

18. The cell culture substrate according to claim 3, wherein the hydrophobic segment is obtainable by polymerizing a monomer represented by the following Formula (1):

[Chem. 1]

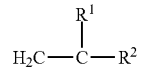

(1)

wherein in Formula (1), $R^1$ represents a hydrogen atom or a methyl group; and $R^2$ represents any one of a phenyl group, a carboxyalkyl group having an alkyl with 1 to 8 carbon atoms, a carboxyaralkyl group having an aralkyl with 7 or 8 carbon atoms, a group represented by the following Formula (2), or a group represented by the following Formula (3):

[Chem. 2]

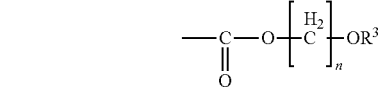

(2)

wherein in Formula (2), n represents 2 or 3; and $R^3$ represents an alkyl group having 1 to 3 carbon atoms,

[Chem. 3]

(3)

wherein in Formula (3), $R^4$ and $R^5$ each independently represent a hydrogen atom or an alkyl group having 1 to 6 carbon atoms; and the total number of carbon atoms of $R^4$ and $R^5$ is 5 or more.

19. The cell culture substrate according to claim 3, further comprising at least one protein selected from gelatin, collagen, and/or albumin on the cell culture substrate.

20. The cell culture substrate according to claim 3, which is a dry cell culture substrate.

* * * * *